United States Patent
Crozier et al.

(10) Patent No.: US 12,327,619 B1
(45) Date of Patent: Jun. 10, 2025

(54) METHOD, APPARATUS, AND COMPUTER PROGRAM PRODUCT FOR GENERATING SUMMARY DATA OBJECTS

(71) Applicant: McKesson Corporation, Irving, TX (US)

(72) Inventors: Keith Crozier, North Kingstown, RI (US); Elizabeth Kaye, Suwanee, GA (US)

(73) Assignee: McKesson Corporation, Irving, TX (US)

( * ) Notice: Subject to any disclaimer, the term of this patent is extended or adjusted under 35 U.S.C. 154(b) by 316 days.

(21) Appl. No.: 17/718,684

(22) Filed: Apr. 12, 2022

(51) Int. Cl.
*G16H 10/60* (2018.01)
*G06Q 40/08* (2012.01)

(52) U.S. Cl.
CPC ............ *G16H 10/60* (2018.01); *G06Q 40/08* (2013.01)

(58) Field of Classification Search
CPC ............................. G16H 10/60; G06Q 40/08
See application file for complete search history.

(56) References Cited

U.S. PATENT DOCUMENTS

| | | | | |
|---|---|---|---|---|
| 6,615,181 B1 * | 9/2003 | Segal | ............ | G06Q 40/08 705/4 |
| 6,684,190 B1 * | 1/2004 | Powers | ............ | G06Q 40/06 705/36 R |
| 6,735,569 B1 * | 5/2004 | Wizig | ............ | G06Q 10/1057 705/2 |
| 6,986,075 B2 * | 1/2006 | Ackaret | ............ | G06F 11/2094 714/E11.089 |
| 7,072,840 B1 * | 7/2006 | Mayaud | ............ | G16H 20/13 600/301 |
| 7,127,407 B1 * | 10/2006 | Averill | ............ | G16H 10/40 705/2 |
| 7,287,031 B1 * | 10/2007 | Karpf | ............ | G06Q 10/10 |
| 7,337,123 B2 * | 2/2008 | Dvorak | ............ | G16H 40/20 709/204 |
| 7,624,028 B1 * | 11/2009 | Brown | ............ | G06Q 40/08 600/300 |
| 7,640,175 B1 * | 12/2009 | Prasad | ............ | G06Q 40/08 705/3 |
| 7,698,155 B1 * | 4/2010 | Prasad | ............ | G16H 20/10 705/3 |
| 7,711,577 B2 * | 5/2010 | Dust | ............ | G06Q 40/08 705/2 |

(Continued)

OTHER PUBLICATIONS

Braunstein_2018_Chapter_1-Chapter_13.*

*Primary Examiner* — Michael I Ezewoko
(74) *Attorney, Agent, or Firm* — ALSTON & BIRD LLP

(57) ABSTRACT

A method, apparatus and computer program product are provided for generating summary data objects, comprised of data from a plurality of source systems. The summary data objects may be provided via an application programming interface (API), that enables a requesting computer to further process, analyze, and/or display certain data. A service provider computer may utilize vaccination data obtained from healthcare claims transmitted by various source systems for the purpose of claim routing, processing, and adjudication, and leverage the data to provide the summary data objects to different requesting computers operating as vaccination verification systems. Various entities may engage the requesting computer to improve the process of verifying electronic vaccination records.

15 Claims, 2 Drawing Sheets

(56) References Cited

U.S. PATENT DOCUMENTS

| | | | | |
|---|---|---|---|---|
| 7,739,124 B1* | 6/2010 | Walker | G06Q 30/0222 | 705/14.23 |
| 7,797,172 B2* | 9/2010 | Fitzgerald | G06Q 40/02 | 705/4 |
| 7,953,615 B2* | 5/2011 | Aquila | G06Q 40/08 | 705/2 |
| 8,036,916 B2* | 10/2011 | Dust | G06Q 30/02 | 705/2 |
| 8,316,263 B1* | 11/2012 | Gough | G06F 11/008 | 706/21 |
| 8,489,420 B2* | 7/2013 | Dust | G06Q 10/10 | 705/2 |
| 8,707,105 B2* | 4/2014 | Grube | G06F 16/972 | 714/48 |
| 8,712,796 B2* | 4/2014 | Moore | G06Q 10/0637 | 705/2 |
| 9,141,457 B1* | 9/2015 | Ma | G06F 11/008 | |
| 9,678,817 B1* | 6/2017 | Hasbun Pacheco | G06F 11/0727 | |
| 10,095,883 B2* | 10/2018 | Antonatos | G06F 11/3006 | |
| 10,157,090 B2* | 12/2018 | Hasbun Pacheco | G06F 11/0727 | |
| 10,268,688 B2* | 4/2019 | Dubbels | G06F 16/2453 | |
| 10,325,069 B2* | 6/2019 | Dust | G16H 40/20 | |
| 10,622,106 B2* | 4/2020 | Dust | G16H 20/10 | |
| 10,747,898 B2* | 8/2020 | Cai | G06F 21/316 | |
| 11,482,313 B2* | 10/2022 | Dust | G16H 20/10 | |
| 11,783,079 B2* | 10/2023 | Bastide | G06F 16/212 | 726/28 |
| 2002/0082480 A1* | 6/2002 | Riff | G16H 40/67 | 600/300 |
| 2002/0087355 A1* | 7/2002 | Rowlandson | A61B 5/0006 | 705/2 |
| 2002/0103680 A1* | 8/2002 | Newman | G06Q 40/02 | 705/4 |
| 2002/0111826 A1* | 8/2002 | Potter | G06Q 30/02 | 705/2 |
| 2002/0116221 A1* | 8/2002 | Fields | G16H 70/20 | 705/2 |
| 2002/0120187 A1* | 8/2002 | Eiffert | G16H 50/20 | 600/407 |
| 2002/0123906 A1* | 9/2002 | Goetzke | G16H 50/20 | 705/2 |
| 2002/0133386 A1* | 9/2002 | Chishti | G16H 40/20 | 705/7.29 |
| 2002/0143680 A1* | 10/2002 | Walters | G06Q 40/06 | 705/36 R |
| 2002/0169635 A1* | 11/2002 | Shillingburg | G16H 20/13 | 705/2 |
| 2002/0173992 A1* | 11/2002 | Dang | G06Q 30/02 | 705/2 |
| 2002/0188484 A1* | 12/2002 | Grover | G06Q 40/08 | 705/4 |
| 2002/0194033 A1* | 12/2002 | Huff | G06Q 40/02 | 705/4 |
| 2003/0011646 A1* | 1/2003 | Levine | G16H 40/20 | 715/848 |
| 2003/0018240 A1* | 1/2003 | Goetzke | G16H 50/50 | 600/300 |
| 2003/0046113 A1* | 3/2003 | Johnson | G16H 20/00 | 705/3 |
| 2003/0060688 A1* | 3/2003 | Ciarniello | G16H 50/70 | 600/300 |
| 2003/0097185 A1* | 5/2003 | Goetzke | G16H 50/20 | 700/1 |
| 2003/0101075 A1* | 5/2003 | Ban | G16H 70/60 | 705/2 |
| 2003/0126101 A1* | 7/2003 | Rao | G16H 50/50 | 706/12 |
| 2003/0163349 A1* | 8/2003 | Ho | G16H 20/10 | 702/81 |
| 2003/0167189 A1* | 9/2003 | Lutgen | G16H 70/60 | 705/3 |
| 2003/0195771 A1* | 10/2003 | Fitzgerald | G06Q 40/08 | 705/40 |
| 2003/0216937 A1* | 11/2003 | Schreiber | G16H 50/30 | 705/2 |
| 2003/0216946 A1* | 11/2003 | Ferraro | G06Q 40/02 | 705/4 |
| 2004/0006488 A1* | 1/2004 | Fitall | G01S 7/52036 | 705/2 |
| 2004/0064341 A1* | 4/2004 | Langan | G16H 15/00 | 705/2 |
| 2004/0083125 A1* | 4/2004 | Almeida | G06Q 30/06 | 705/4 |
| 2004/0103001 A1* | 5/2004 | Mazar | G16H 50/50 | 600/300 |
| 2004/0111291 A1* | 6/2004 | Dust | G16H 40/20 | 705/2 |
| 2004/0143446 A1* | 7/2004 | Lawrence | G06Q 40/08 | 705/2 |
| 2006/0235280 A1* | 10/2006 | Vonk | G16H 50/20 | 600/300 |
| 2007/0011134 A1* | 1/2007 | Langseth | G06F 16/254 | |
| 2010/0217625 A1* | 8/2010 | Dust | G06Q 30/02 | 705/2 |
| 2012/0010898 A1* | 1/2012 | Dust | G16H 10/60 | 705/2 |
| 2013/0346096 A1* | 12/2013 | Moore | G06Q 40/00 | 705/2 |
| 2014/0200907 A1* | 7/2014 | Dust | G16H 40/20 | 705/2 |
| 2014/0249843 A1* | 9/2014 | Dust | G06Q 10/00 | 705/2 |
| 2017/0235887 A1* | 8/2017 | Cox | G16H 10/60 | 705/3 |
| 2018/0025179 A1* | 1/2018 | Antonatos | G06F 16/2228 | 726/27 |
| 2018/0322119 A1* | 11/2018 | Dubbels | G06F 16/93 | |
| 2019/0163813 A1* | 5/2019 | Tomlinson | G06F 16/3334 | |
| 2019/0164092 A1* | 5/2019 | Argyros | G06F 3/0482 | |
| 2019/0197061 A1* | 6/2019 | Dubbels | G06F 40/169 | |
| 2019/0197062 A1* | 6/2019 | Dubbels | G06F 40/237 | |
| 2019/0266042 A1* | 8/2019 | Dust | G06Q 40/08 | |
| 2021/0200894 A1* | 7/2021 | Bastide | G06F 16/212 | |
| 2022/0006873 A1* | 1/2022 | Rogynskyy | G06F 16/906 | |
| 2022/0262472 A1* | 8/2022 | Dust | G16H 20/00 | |
| 2023/0409744 A1* | 12/2023 | Bastide | G06F 21/6245 | |

* cited by examiner

METHOD, APPARATUS, AND COMPUTER PROGRAM PRODUCT FOR GENERATING SUMMARY DATA OBJECTS

TECHNOLOGICAL FIELD

Embodiments of the present invention relate generally to electronic messages, and more particularly, to methods, apparatuses, and computer program products for generating summary data objects based on received electronic messages.

BACKGROUND

Electronic messages are frequently transmitted and routed for processing by various computers. Some service providers have access to a significant amount of data pertaining to electronic messages received and routed for a variety of purposes. Such data may be stored and utilized only for a particular use, and is often not accessible by other systems, nor formatted in a useful way. Personal healthcare and medical data have long been notorious for being difficult to manage. Privacy laws, multiple sources using different architectures and underlying systems, amongst other challenges inhibits data integration and leverage of the medical data by other systems.

In light of development of vaccines for the coronavirus (COVID-19), many organizations, events, travel carriers, and/or the like began enforcing vaccination requirements for attendees. Attendees are often required to provide a vaccination card, which could be the subject of fraudulent use and clerical errors. Various attempts have been made to streamline the electronic provision of vaccination records, but many such methods require downloading of vaccine records from one system and uploading to another. Some systems provide a renderable vaccination record, but some may only display proof of a single record, may be provided only from a single source, or are not in a format easily recognized or readable by the requesting party. Some patients receive different doses of a vaccination from different sources, and therefore must handle multiple different records obtained from various systems and in different formats, and track and provide the records to the requesting party.

BRIEF SUMMARY

Methods, apparatuses, and computer program products are therefore provided for generating summary data objects from retrieved records such as those relating to healthcare claims, including but not limited to prescription claims and/or medical claims. A service provider computer that operates as a switch for receiving, processing, routing, and routing of responses for a plurality of healthcare providers, pharmacies and prescription benefit plans can leverage healthcare claim data pertaining to vaccinations in a non-routine way to facilitate vaccination verification via an application programming interface (API). The API can be utilized by any system to obtain the desired vaccination data, perform additional analyses, and/or format the data for display. Different vaccination verifiers can utilize and present the data obtained from the API as desired by their organization.

An apparatus is provided, comprising at least one processor and at least one memory including computer program code, the at least one memory and the computer program code configured to, with the processor, cause the apparatus to at least receive a plurality of electronic messages from a plurality of source systems, wherein each electronic message comprises at least an entity identifier and a product identifier. The at least one memory and the computer program code configured to, with the processor, cause the apparatus to, for each of the plurality of the electronic messages, insert a record into a database table comprising at least a column of entity identifiers and a column of product identifiers, wherein the database table comprises records from the plurality of source systems. The at least one memory and the computer program code are further configured to receive, from a requesting computer, a summary request comprising at least one summary request parameter that comprises at least one entity identifier. In response to the summary request, the at least one memory and the computer program code are further configured to retrieve records from the database table according to the at least one summary request parameters that comprises the at least one entity identifier. The at least one memory and the computer program code are further configured to generate a summary data object comprising the retrieved records, and cause transmission of the summary data object to the requesting computer.

The summary request is transmitted via an application programing interface (API) exposed to the requesting computer for interfacing with the apparatus. At least one of the plurality of source systems comprise one or more pharmacy computers, the electronic messages comprise electronic prescription claims, and the respective entity identifier identifies a patient having received a vaccine identified by the respective product identifier. The at least one of the plurality of source systems comprise one or more healthcare provider computers, the electronic messages comprise electronic medical claims, and the respective entity identifier identifies a patient having received a vaccine identified by the respective product identifier. The summary data object comprises any of a vaccination date, a vaccination series or dose, vaccine manufacturer, vaccine lot number, or a vaccination location. The at least one memory and the computer program code are further configured to, with the processor, cause the apparatus to at least cause display of data from the summary data object via a remote user interface.

The apparatus is a service provider computer configured to facilitate routing, processing, and payment of healthcare claims configured as the electronic messages. The at least one of the plurality of source systems comprises at least one of an electronic health record (EHR) system or a vaccination registry.

A method is provided, including receiving a plurality of electronic messages from a plurality of source systems, wherein each electronic message comprises at least an entity identifier and a product identifier. The method further includes, for each of the plurality of the electronic messages, inserting a record into a database table comprising at least a column of entity identifiers and a column of product identifiers, wherein the database table comprises records from the plurality of source systems. The method further includes, receiving, from a requesting computer, a summary request comprising at least one summary request parameter that comprises at least one entity identifier, and in response to the summary request, retrieving records from the database table according to the at least one summary request parameters that comprises the at least one entity identifier. The method further includes, with at least a processor, generating a summary data object comprising the retrieved records, and cause transmission of the summary data object to the requesting computer. The summary request is transmitted via an application programing interface (API) exposed to the requesting computer. The at least one of the plurality of source systems comprise one or more pharmacy computers, the electronic messages comprise electronic prescription claims, and the respective entity identifier identifies a patient having received a vaccine identified by the respective product identifier. The at least one of the plurality of source systems comprise one or more healthcare provider computers, the electronic messages comprise electronic medical claims, and the respective entity identifier identifies a patient having received a vaccine identified by the respective product identifier. The method may further include causing display of data from the summary data object via a remote user interface. The method may be performed by a service provider computer configured to facilitate routing, processing, and payment of healthcare claims configured as the electronic messages.

A computer program product is provided, comprising at least one non-transitory computer-readable storage medium having computer-executable program code instructions stored therein, the computer-executable program code instructions comprising program code instructions to receive a plurality of electronic messages from a plurality of source systems, wherein each electronic message comprises at least an entity identifier and a product identifier. for each of the plurality of the electronic messages, insert a record into a database table comprising at least a column of entity identifiers and a column of product identifiers, wherein the database table comprises records from the plurality of source systems. The computer-executable program code instructions further include program code instructions to receive, from a requesting computer, a summary request comprising at least one summary request parameter that comprises at least one entity identifier. In response to the summary request, computer-executable program code instructions comprising program code instructions to retrieve records from the database table according to the at least one summary request parameters that comprise the at least one entity identifier, generate a summary data object comprising the retrieved records, and cause transmission of the summary data object to the requesting computer.

An apparatus is provided, with means for including receiving a plurality of electronic messages from a plurality of source systems, wherein each electronic message comprises at least an entity identifier and a product identifier. The apparatus further includes means, for each of the plurality of the electronic messages, for inserting a record into a database table comprising at least a column of entity identifiers and a column of product identifiers, wherein the database table comprises records from the plurality of source systems. The apparatus further includes means for, receiving, from a requesting computer, a summary request comprising at least one summary request parameter that comprises at least one entity identifier, and in response to the summary request, means for retrieving records from the database table according to the at least one summary request parameters that comprises the at least one entity identifier. The apparatus further includes means for generating a summary data object comprising the retrieved records, and cause transmission of the summary data object to the requesting computer. The apparatus further includes transmitting the summary request via an application programing interface (API) exposed to the requesting computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
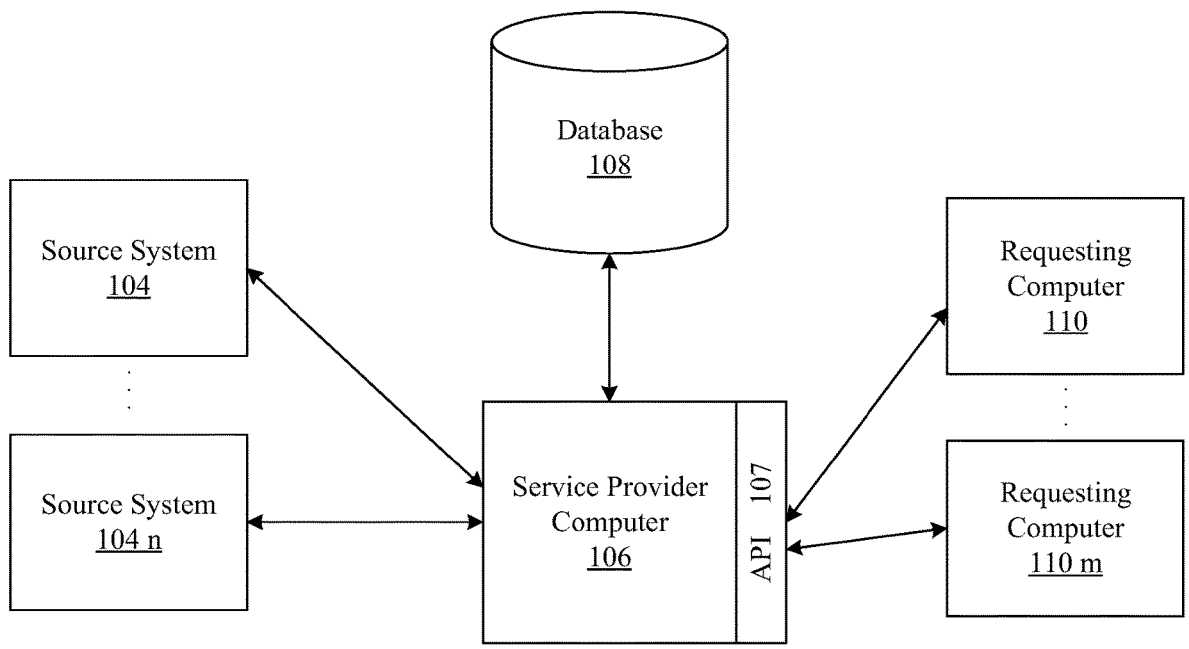
Figure 2:
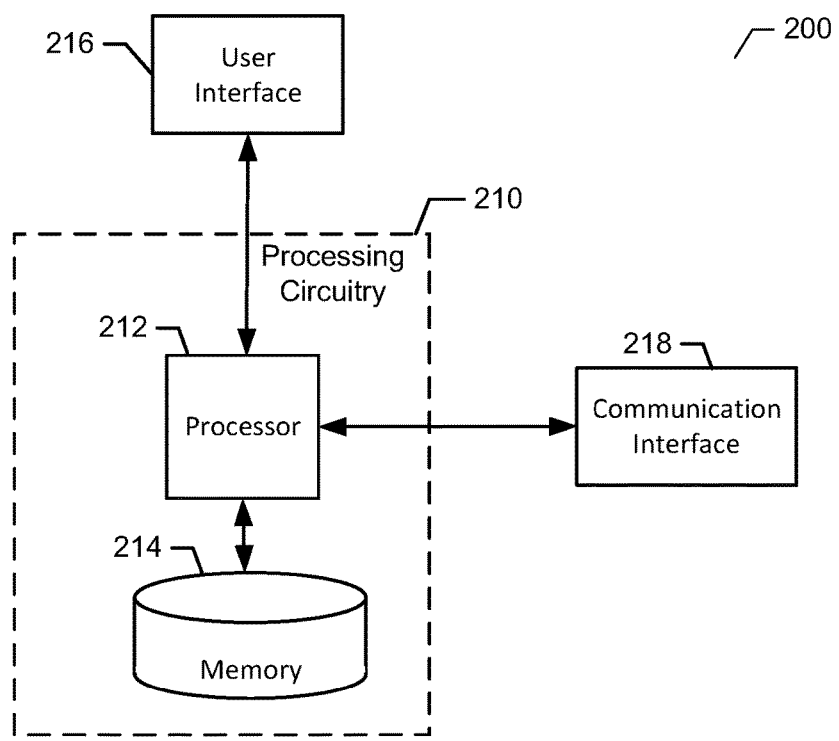
Figure 3:
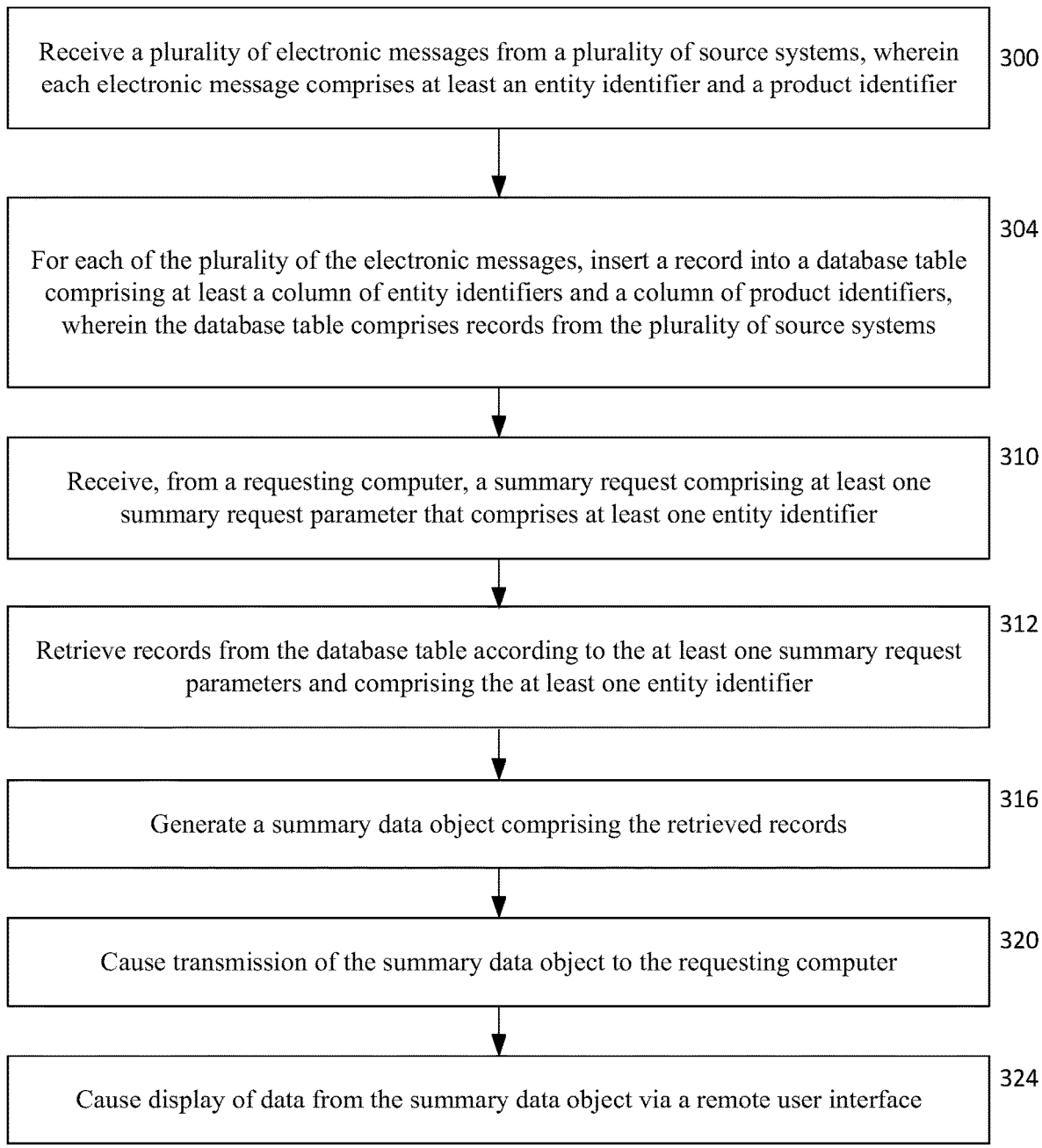

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIG. 3 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to practice certain example embodiments. Numerous source systems 104-104n, each of which may be referred to herein as a source system 104, may be present in the system. Different types of source systems may be present, such as but not limited to a pharmacy computer, healthcare provider computer, EHR system, vaccination registries, any other provider of vaccination records, and/or the like.

A source system configured as a pharmacy computer may be associated with a pharmacy or pharmacy network to facilitate the filling of prescriptions, transmitting prescription claims, prescription inquiries, and/or prescription refill requests to a service provider computer 106, and/or the like. In this regard the source system may include a point-of-sale device of a pharmacy, and/or a server of the pharmacy in communication therewith. In this regard, a source system configure as a pharmacy computer may route prescription claims associated with vaccinations to the service provider computer 106.

When the source system is configured as a healthcare provider computer, the source system may be configured to facilitate interactions between physicians, healthcare providers and other staff associated therewith, with the service provider computer 106. For example, the healthcare provider computer may facilitate the submission of medical claims toward an adjudicator or other payer, via the service provider computer 106. In this regard, a medical claim representative of a vaccination administered by the healthcare provider may be transmitted to the service provider computer 106 (along with claims for other services administered by the healthcare provider).

In certain embodiments, a source system 104 may include an electronic healthcare record (EHR) system and/or other system associated with record keeping of personal healthcare data such as that relating to patient visits. For example, the EHR system may track data collected during a patient encounter, noted symptoms, lab results, vital signs, physician notes, information regarding vaccinations administered, and/or the like.

In certain embodiments, a source system 104 may include a registry of vaccination records and/or the like. In this regard, any such system configured to track vaccination records may further provide an Application Programming Interface (API) to enable other systems to access the respective system and obtain vaccination records. The service provider computer 106 may therefore access one or more vaccination registries, other systems for tracking vaccination records, and/or the like. In certain embodiments, the service provider computer 106 may access multiple source systems 104 configured as vaccination registries, such as different source systems 104 for each state, or one or more states.

The service provider computer 106 may include, but is not limited to, a processor-driven device that is configured for receiving, processing, and responding to electronic messages from a source system 104. In certain embodiments, the service provider computer 106 is configured as a switch, processor, and router of healthcare and/or prescription related messages, transactions, and/or claims. The service provider computer 106 may process such messages by optionally applying pre-edits to a healthcare claim, and/or generating a prescription claim from data in a prescription transaction and/or the like. The service provider computer 106 may then route a corresponding claim toward an adjudication computer associated with a prescription benefit plan (PBM) and/or adjudicator, monitor for a response, and provide the associated response to the source system 104 in real-time or near-time relative to receipt of the healthcare claim from the source system 104. The service provider computer 106 may route prescription inquiries to various adjudication computers to obtain responses regarding prescription benefits and out of pocket patient prices. In certain exemplary embodiments, the service provider computer 106 may be configured as or may comprise a switch or router that evaluates, modifies, reformats, generates, and/or routes healthcare claims. In this regard, the service provider computer 106 may leverage its access to prescription claim and medical claim data to obtain records of vaccinations, such as those occurring at pharmacies and/or healthcare providers.

In certain embodiments, the service provider computer 106 may store data associated with EHR systems, and/or host and facilitate certain EHR systems such that the service provider computer 106 has further access to vaccination records stored therein.

The service provider computer 106 may be further improved upon by integrating the service provider computer 106 with vaccination registries, such as but not limited to state vaccination registries, and/or other source systems 104 that may be configured to provide data relating to vaccination records.

The database 108 may comprise any computing device configured to store data, such as prescription claims received by the service provider computer via a source system 104. In certain embodiments, selected records may be stored in database 108. For example, the service provider computer 106 may store healthcare claim data indicative of a vaccination, and/or may format data in tables based on a particular virus, disease, and/or other condition with which the vaccination is associated. In certain embodiments, the service provider computer 106 may poll EHR systems and/or vaccination registries via an API, and build upon the vaccination records stored in database 108. Accordingly the service provider computer 106 compiles vaccination records from multiple disparate sources and enables efficient access, and possibly a single point of access (e.g., via an API of the service provider computer 106) for other systems to obtain the vaccination records and verify an individual's vaccination status. According to certain embodiments, the database 108 may be maintained or operated by the service provider computer 106, as it functions as a switch for routing and processing certain healthcare related transactions, claims and/or messages submitted by at least some of the various source systems 104, such as a pharmacy computers, healthcare provider computers, and/or EHR systems. It will be appreciated that the service provider computer 106 may communicate with many different pharmacy computers, such as those operating independently of one another, but that are nevertheless integrated with the service provider computer. Similarly, the service provider computer 106 may receive data from many different healthcare provider computers, including those that operate independently of one another, but that are integrated with the service provider computer 106. The service provider computer 106 may be further configured to communicate with multiple EHR systems that operate independently of each other, and multiple vaccination registries that operate independently of each other.

An application programming interface (API) 107 of the service provider computer 106 may be provided as an interface from any number of requesting computers 110-110*m*, referred to herein as a requesting computer 110. A requesting computer 110 may include any system or computer configured to request vaccination verification and/or vaccination records from the service provider computer 106. For example, the requesting computer 110 may include a service in contractual agreement with various entities such as event planners, airlines, jurisdictions, and/or the like to provide the entities with vaccination records of customers and/or visitors so that vaccination statuses may be verified according to a respective entity's policies.

The API 107 may therefore include computer program code implemented as an endpoint exposed to authorized systems, such as requesting computers 110. The API 107 may further include computer program code, that when executed by the service provider computer 106, in response to invocation of the API 107, retrieves data from the database 108 based on parameters passed via the API 107 from the source system 104, performs any additional edits and/or formatting, and provides the requested data to the requesting computer 110. The requesting computer 110 may further manipulate the data and/or cause the data to be displayed. In some embodiments, the API 107 may control display of the data via the requesting computer 110. Numerous variations may be contemplated.

Referring now to FIG. 2, apparatus 200 is a computing device(s) configured for implementing source system 104, service provider computer 106, requesting computer 110, and/or database 108, according to example embodiments.

Apparatus 200 may at least partially or wholly embody or be embodied by any of the source system 104, service provider computer 106, database 108, and/or requesting computer 110. Apparatus 200 may therefore implement any of the source system 104, service provider computer 106, and/or requesting computer 110, in accordance with some example embodiments, or may be implemented as a distributed system that includes any of the source system 104, service provider computer 106, database 108, requesting computer 110, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in some components, such as the service provider computer 106, and/or requesting computer 110, for example. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the source system 104, service provider computer 106, database 108, requesting computer 110, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as source system 104, service provider computer 106, database 108, requesting computer 110, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a source system 104, and/or requesting computer 110. Memory 214 may further include reconciliation tables for tracking the healthcare claims and/or prescription claims and reconciling them with responses received from adjudication computers. The memory 214 may further comprise a database, such as database 108, comprising historical claims, such as but not limited to those relating to vaccinations administered at numerous pharmacies and/or providers.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications, including but not limited to API 107, may be stored for execution by the processor 212 to carry out the functionality associated with respective applications. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the source system 104, the user interface 216 may, in some example embodiments, provide means for user entry of details relating to the administration of a vaccine and the associated healthcare claim. The user interface 216 may be further configured to display or provide responses relating to patient pay amounts for vaccination, such as when apparatus 200 is implemented as a source system 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of source system 104, service provider computer 106, requesting computer 110, API 107, database 108, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., source system 104, service provider computer 106, API 107, requesting computer 110, database 108, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

FIG. 3 is a flowchart illustrating example operations of an apparatus 200, according to some example embodiments. The operations of FIG. 3 may be performed by apparatus 200, such as with the service provider computer 106, and/or the like.

Accordingly, as shown by operation 300 of FIG. 3, apparatus 200 may include means, such as processor 212, memory 214, communication interface 218, and/or the like, for receiving a plurality of electronic messages from a plurality of source systems, wherein each electronic message comprises at least an entity identifier and a product identifier. The electronic messages may include prescription claims transmitted from source systems, such as pharmacy computers operative in a network and in communication with the service provider computer 106, such that the respective entity identifier identifies a patient having received a vaccine identified by the respective product identifier.

In certain embodiments, one or more of the electronic messages comprise one or more medical claims, such that the electronic message may be indicative of patient visits at a healthcare provider, which may further include a record of vaccination administration. In this regard, the respective entity identifier identifies a patient having received a vaccine identified by the respective product identifier.

In certain embodiments, one or more of the electronic messages comprise EHR data received from an EHR system, and/or vaccination registry data such that may be received from a vaccination registry.

An entity identifier may include any identifying information of a patient (e.g., name, address, date of birth (DOB), patient identifying number and/or the like), and a product identifier includes an identifier of a vaccine, such as a national drug code (NDC).

Electronic messages such as prescription claims and/or medical claims received respectively from pharmacy computers and/or healthcare provider computers, may further include information regarding a benefit plan, such as but not limited to PCN, BIN, and/or member identifier. The electronic messages may be transmitted to the service provider computer 106 as part of a routine process to initiate adjudication (and payment by a PBM, insurance provider, and/or other payer) for expenses associated with a healthcare visit, prescription, or vaccination, but are further processed in a non-routine and unconventional way, as described in further detail below. The service provider computer 106, functioning as a switch for many pharmacy computers and various PBMs, can therefore leverage the numerous electronic messages routed to it for the purpose of facilitating the processing and payment of claims.

As shown by operation 304, apparatus 200 may include means, such as processor 212, memory 214, communication interface 218, and/or the like, for each of the plurality of the electronic messages, inserting a record into a database table comprising at least a column of entity identifiers and a column of product identifiers, wherein the database table comprises records from the plurality of source systems. In this regard, the service provider computer 106 maintains the database 108 such that it can subsequently and efficiently access vaccination records, such as by patient and/or by vaccination type (and/or related virus and/or disease). Additional data may be stored in the database 108 with the vaccination records, including but not limited to location of vaccination administration, date administered, dose number, manufacturer, lot number, dosage, and/or the like. The database 108 may be updated in real-time or near real-time relative to the receipt of corresponding messages from the source systems 104 (e.g., as pharmacy computers and/or healthcare provider computers transmit claims for processing and adjudications), as the claims are often processed in real-time or near real-time for the purposes of insurance claim processing and/or pricing while the patient is in the pharmacy receiving their vaccine, or during a patient encounter that includes a vaccination. Additionally or alternatively, a historical claim database may be accessed on a routine basis to reconcile vaccination records with newly received, or recently received claims.

As another example, electronic messages such as those received in response to an API call to a vaccination registry may be received on a routine basis. For example, the service provider computer 106 may call the API on a nightly basis and/or other time internal, and import batches of vaccination records into database 108. Electronic messages received from an EHR system may be similarly imported, and/or accessed by the service provider computer 106 such as when the service provider computer 106 functions as a facilitator or record keeper for the EHR system.

In any event, the database 108 is populated with vaccination records from a plurality of disparate source systems 104, including but not limited to pharmacy computers, healthcare provider computers, EHR systems, and/or vaccination registries.

As shown by operation 310, apparatus 200 may include means, such as processor 212, memory 214, communication interface 218, and/or the like, for receiving, from a requesting computer 110, a summary request comprising at least one summary request parameter that comprises at least one entity identifier. A request may be received via API 107, and may include any number of parameters, for example, including but not limited to an entity identifier identifying the patient and/or individual for which a vaccination record is requested, such as but not limited to first name, last name, date of birth, zip code, and/or the like. As another example, a summary request may include any indicator of a vaccine type and/or related virus and/or disease, such but not limited to COVID-19. Other parameters may include a date range, other patient identifying information, and/or the like.

As shown by operation 312, apparatus 200 may include means, such as processor 212, memory 214, communication interface 218, and/or the like, for retrieving records from the database table according to the at least one summary request parameter including the at least one entity identifier. For example, the service provider computer 106 may query the database 108 to determine records that match the parameters passed via the API 107. The records may therefore have originated from any number of disparate source systems 104, including pharmacy computers, healthcare providers, EHRs, vaccination registries, and/or the like.

In operation 316, apparatus 200 may include means, such as processor 212, memory 214, communication interface 218, and/or the like, for generating a summary data object comprising the retrieved records. The summary data object may include multiple instances of records, such as but not limited to multiple doses in a series of vaccines related to COVID-19 given to an individual (or group of individuals). As another example, the summary data object may include all records for an individual(s) for a specified time period, or in any of the historical records as far back as the records date.

In certain embodiments, the service provider computer 106 may further define requirements considered for a patient to be fully vaccinated against a certain virus and/or disease, and execute further analyses on the data to determine whether a patient is considered fully vaccinated or not. In this regard, the summary data object may comprise a Boolean flag and/or yes/no indicator indicating whether the patient is fully vaccinated.

As shown by operation 320, apparatus 200 may include means, such as processor 212, memory 214, communication interface 218, and/or the like, for causing transmission of the summary data object to the requesting computer. In this regard, after the summary data object is transmitted via the API 107 and communication interface 218, to the requesting computer 110, the requesting computer 110 can process the summary data object to access individual records in the object, and optionally format, organize and/or display certain data.

As another, example, the requesting computer 110 may analyze data in the summary data object and determine a status or other outcome for display. For example, the requesting computer 110 may access the data to determine if certain predefined requirements are satisfied, such as an individual receiving a certain number of doses of a vaccine, certain number of doses within a specified time period, and/or the like. The requesting computer 110 may utilize the summary data object in a variety of ways. In this regard, the data can be further selected, arranged, and/or displayed according to certain requirements by the entity hosting the event, travel, and/or the like.

As shown by operation 324, apparatus 200 may include means, such as processor 212, memory 214, user interface 216, communication interface 218, and/or the like, for causing display of data from the summary data object via a remote user interface. In addition to or alternative to operation 320, the service provider computer 106 may direct a user interface 216 of the requesting computer 110 to display vaccination details from the summary data object. The service provider computer 106 may direct the requesting computer 110 to display data, such including any of the data described above with respect to operation 320.

Because the service provider computer 106 utilizes prescription claim data and/or medical claim data to generate summary data objects, the service provider computer 106 and recipient systems (such as requesting computer 110) can ensure the integrity and authenticity of the data contained in the summary data objects. Pharmacies and healthcare providers that contract with the service provider computer 106 are obligated to submit only claims for services that occur, and are further obligated to reverse transactions initiated with the service provider computer 106 that were not administered or not fully administered. Healthcare claims are subject to laws, regulations and transaction standards such that the claim data utilized by example embodiments provide higher quality and improved data integrity than a record that is manually created. Therefore, the data provided to the service provider computer 106 may be considered more reliable than data merely uploaded by an individual user to a different system, for example, and more reliable than paper copies of vaccination records which could be incorrect or subject to fraudulent use.

Example embodiments provided herein therefore provide a technical solution to a technical problem presented by requesting computers, such as vaccination verification services and/or entities that utilize the vaccination verification services, not having a streamlined and systematic way to access electronic vaccination data. The integration of a service provider computer 106 with a vast number of different pharmacy computers and healthcare provider computers enables the service provider computer 106 to store, consolidate, and efficiently access requested vaccination data, even if initially sourced from different source systems 104 (e.g., various pharmacy computers, various healthcare provider computers, various EHR systems, and/or various vaccination registries). The use of an API 107 further allows different requesting computers 110 and/or entities contracted with the requesting computer 110 to direct which data is provided, and in what format.

Example embodiments therefore improve upon existing service provider computers 106 by leveraging the prescription claim data and medical claim data, submitted for the purpose of claim adjudication and payment, in a non-routine and unconventional way to provide cohesive vaccination records from multiple sources and source types. Example embodiments further reduce the consumption of processing, memory, and network resources otherwise consumed when patients access multiple individual systems (such as those associated with different pharmacies and different healthcare providers), download records to local storage, and upload the records to a respective vaccination verification system. Example embodiments further reduce the consumption of processing, memory, and network resources otherwise consumed when users of a vaccination verification system and/or entity requesting the vaccination verification system otherwise access multiple individual systems in an effort to retrieve vaccination records for an individual(s).

Example embodiments further improve and streamline the customer experience. For example, the customer doesn't have to go find their vaccination card that may be stored in their house somewhere in order to then upload it into the service, therefore reducing the consumption of network resources to facilitate the uploading. Example embodiments may therefore also reduce the number of people that may abandon the process due to lack of desire to find their vaccination card. Additionally, some people who have lost their vaccination card and don't know how to get a new one. Example embodiments replace the need for individual to produce their vaccination card.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the at least one processor, cause the apparatus to at least:

receive a plurality of electronic prescription claims from a plurality of pharmacy computers and a plurality of electronic medical claims from a plurality of healthcare provider systems, wherein each of the plurality of electronic prescription claims and the plurality of electronic medical claims comprises at least an entity identifier and a product identifier;

transmit the plurality of electronic prescription claims and the plurality of electronic medical claims to one or more adjudication computers;

receive, in real-time relative to transmitting the plurality of electronic prescription claims and the plurality of electronic medical claims, adjudicated responses, associated with the plurality of electronic prescription claims and the plurality of electronic medical claims, from the one or more adjudication computers;

for each of the adjudicated responses associated with the plurality of electronic prescription claims and the plurality of electronic medical claims, insert a record into a database table comprising at least a column of entity identifiers and a column of product identifiers, wherein the database table comprises records from the plurality of pharmacy computers and the plurality of healthcare provider systems, wherein the entity identifiers identify patients having received a vaccine identified by the product identifiers;

receive, from a requesting computer, a summary request comprising at least one summary request parameter that comprises at least one entity identifier; and in response to the summary request,
retrieve records from the database table according to the at least one summary request parameter that comprises the at least one entity identifier;

generate a summary data object comprising the retrieved records; and cause transmission of the summary data object to the requesting computer via an application programming interface (API).

2. The apparatus according to claim 1, wherein the summary data object comprises any of a vaccination date, a vaccination series or dose, vaccine manufacturer, vaccine lot number, or a vaccination location.

3. The apparatus according to claim 1, wherein the at least one memory and the computer program code are configured to, with the at least one processor, cause the apparatus to at least:

cause display of data from the summary data object via a remote user interface.

4. The apparatus according to claim 1, wherein the apparatus is a service provider computer configured to facilitate routing, processing, and payment of the plurality of electronic prescription claims and the plurality of electronic medical claims.

5. The apparatus according to claim 1, wherein the database table further comprises records from an electronic health record (EHR) system and a vaccination registry.

6. A method comprising:

receiving a plurality of electronic prescription claims from a plurality of pharmacy computers and a plurality of electronic medical claims from a plurality of healthcare provider systems, wherein each of the plurality of electronic prescription claims and the plurality of electronic medical claims comprises at least an entity identifier and a product identifier;

transmitting the plurality of electronic prescription claims and the plurality of electronic medical claims to one or more adjudication computers;

receiving, in real-time relative to transmitting the plurality of electronic prescription claims and the plurality of electronic medical claims, adjudicated responses, associated with the plurality of electronic prescription claims and the plurality of electronic medical claims, from the one or more adjudication computers;

for each of the adjudicated responses associated with the plurality of the electronic prescription claims and the plurality of electronic medical claims, inserting a record into a database table comprising at least a column of entity identifiers and a column of product identifiers, wherein the database table comprises records from the plurality of pharmacy computers and the plurality of healthcare provider systems, wherein the entity identifiers identify patients having received a vaccine identified by the product identifiers;

receiving, from a requesting computer, a summary request comprising at least one summary request parameter that comprises at least one entity identifier; and in response to the summary request, retrieving records from the database table according to the at least one summary request parameter that comprises the at least one entity identifier;

with at least a processor, generating a summary data object comprising the retrieved records; and cause transmission of the summary data object to the requesting computer via an application programming interface (API).

7. The method according to claim 6, wherein the summary data object comprises any of a vaccination date, a vaccination series or dose, vaccine manufacturer, vaccine lot number, or a vaccination location.

8. The method according to claim 6, further comprising: causing display of data from the summary data object via a remote user interface.

9. The method according to claim 6, wherein the method is performed by a service provider computer configured to facilitate routing, processing, and payment of the plurality of electronic prescription claims and the plurality of electronic medical claims.

10. The method according to claim 6, wherein the database table further comprises records from an electronic health record (EHR) system and a vaccination registry.

11. A computer program product comprising at least one non-transitory computer-readable storage medium having computer-executable program code instructions stored therein, the computer-executable program code instructions comprising program code instructions to:

receive a plurality of electronic prescription claims from a plurality of pharmacy computers and a plurality of electronic medical claims from a plurality of healthcare provider systems, wherein each of the plurality of electronic prescription claims and the plurality of electronic medical claims comprises at least an entity identifier and a product identifier;

transmit the plurality of electronic prescription claims and the plurality of electronic medical claims to one or more adjudication computers;

receive, in real-time relative to transmitting the plurality of electronic prescription claims and the plurality of electronic medical claims, adjudicated responses, associated with the plurality of electronic prescription claims and the plurality of electronic medical claims, from the one or more adjudication computers;

for each of the adjudicated responses associated with the plurality of electronic prescription claims and the plurality of electronic medical claims, insert a record into a database table comprising at least a column of entity identifiers and a column of product identifiers, wherein the database table comprises records from the plurality of pharmacy computers and the plurality of healthcare provider systems, wherein the entity identifiers identify patients having received a vaccine identified by the product identifiers;

receive, from a requesting computer, a summary request comprising at least one summary request parameter that comprises at least one entity identifier; and in response to the summary request, retrieve records from the database table according to the at least one summary request parameter that comprises the at least one entity identifier;

generate a summary data object comprising the retrieved records; and cause transmission of the summary data object to the requesting computer via an application programming interface (API).

12. The computer program product according to claim 11, wherein the summary data object comprises any of a vaccination date, a vaccination series or dose, vaccine manufacturer, vaccine lot number, or a vaccination location.

13. The computer program product according to claim 11, wherein the computer-executable program code instructions further comprise program code instructions to:

cause display of data from the summary data object via a remote user interface.

14. The computer program product according to claim 11, wherein the computer program product is stored by a service provider computer configured to facilitate routing, processing, and payment of the plurality of electronic prescription claims and the plurality of electronic medical claims.

15. The computer program product according to claim 11, wherein the database table further comprises records from an electronic health record (EHR) system and a vaccination registry.

\* \* \* \* \*